United States Patent
Hennigan

(10) Patent No.: US 10,988,432 B2
(45) Date of Patent: Apr. 27, 2021

(54) PROCESS FOR THE CO-PRODUCTION OF ACETIC ACID AND ACETIC ANHYDRIDE

(71) Applicant: Ineos Acetyls UK Limited, Lyndhurst (GB)

(72) Inventor: Sean Anthony Hennigan, East Yorkshire (GB)

(73) Assignee: Ineos Acetyls UK Limited, Lyndhurst (GB)

( * ) Notice: Subject to any disclaimer, the term of this patent is extended or adjusted under 35 U.S.C. 154(b) by 406 days.

(21) Appl. No.: 14/773,399

(22) PCT Filed: Mar. 6, 2014

(86) PCT No.: PCT/EP2014/054398
§ 371 (c)(1),
(2) Date: Sep. 8, 2015

(87) PCT Pub. No.: WO2014/135664
PCT Pub. Date: Sep. 12, 2014

(65) Prior Publication Data
US 2016/0016878 A1    Jan. 21, 2016

(30) Foreign Application Priority Data
Mar. 7, 2013 (EP) ..................... 13158258

(51) Int. Cl.
| C07C 51/56 | (2006.01) |
| C07C 51/12 | (2006.01) |
| C07C 51/42 | (2006.01) |
| C07C 51/44 | (2006.01) |
| C07C 51/573 | (2006.01) |

(52) U.S. Cl.
CPC .............. *C07C 51/56* (2013.01); *C07C 51/12* (2013.01); *C07C 51/42* (2013.01); *C07C 51/44* (2013.01); *C07C 51/573* (2013.01)

(58) Field of Classification Search
CPC ..................................... C07C 51/10
USPC ....................................... 562/517
See application file for complete search history.

(56) References Cited

U.S. PATENT DOCUMENTS

| 3,927,078 | A |  | 12/1975 | Lapporte et al. |
| 4,046,807 | A |  | 9/1977 | Kuckertz |
| 4,115,444 | A |  | 9/1978 | Rizkalla |
| 4,252,741 | A |  | 2/1981 | Porcelli et al. |
| 4,374,070 | A |  | 2/1983 | Larkins et al. |
| 4,430,273 | A |  | 2/1984 | Erpenbach et al. |
| 4,559,183 | A |  | 12/1985 | Hewlett |
| 4,661,619 | A | * | 4/1987 | Alper ................ C07C 51/10 560/100 |
| 4,717,454 | A |  | 1/1988 | Erpenbach et al. |
| 5,003,104 | A |  | 3/1991 | Paulik et al. |
| 5,227,520 | A |  | 7/1993 | Cooper |
| 5,292,948 | A |  | 3/1994 | Zoeller et al. |
| 5,763,654 | A | * | 6/1998 | Jones ................ C07C 51/12 562/517 |
| 5,922,911 | A |  | 7/1999 | Jones et al. |
| 6,130,355 | A | * | 10/2000 | Jones ................ C07C 51/12 562/517 |
| 6,541,666 | B2 |  | 4/2003 | Allan et al. |
| 7,737,298 | B2 | * | 6/2010 | Kline ................ C07C 51/12 562/517 |
| 9,115,071 | B2 |  | 8/2015 | Shimizu et al. |
| 2012/0123156 | A1 | * | 5/2012 | Wellman, Jr. ........ C07C 51/54 562/517 |

FOREIGN PATENT DOCUMENTS

| CH |  | 152249 | A |  | 1/1932 |  |
| EP |  | 0 029 514 |  |  | 6/1981 |  |
| EP |  | 0087870 | B1 |  | 4/1985 |  |
| EP |  | 0087869 | B1 |  | 7/1986 |  |
| EP |  | 0 566 370 | A2 |  | 10/1993 |  |
| EP |  | 2029514 | B1 | * | 6/2006 | ............. C07C 51/12 |
| EP |  | 2029514 | A2 | * | 3/2009 | ............. C07C 51/12 |
| EP |  | 2029514 | B1 | * | 10/2014 | ............. C07C 51/12 |
| EP |  | 2029514 | B1 | * | 10/2014 | ............. C07C 51/12 |
| WO | WO 2007/145795 | A2 |  |  | 12/2007 |  |

* cited by examiner

Primary Examiner — Clinton A Brooks
(74) Attorney, Agent, or Firm — McDonnell Boehnen Hulbert & Berghoff LLP

(57) ABSTRACT

Continuous process for co-production of acetic acid and acetic anhydride by contacting carbon monoxide with a liquid reaction composition containing methyl acetate, dimethyl ether or a mixture thereof, a Group VIII metal catalyst, methyl iodide, acetic acid, acetic anhydride, and water in a concentration of 0.1 wt % or less, withdrawing liquid reaction composition from the reaction zone, introducing at least a portion thereof into a flash separation zone, and removing from the flash separation zone a vapor fraction containing acetic anhydride, acetic acid and methyl iodide and a liquid fraction containing acetic anhydride, and Group VIII metal catalyst. The liquid reaction composition and the withdrawn liquid reaction composition introduced into the flash separation zone contains a Group IA and/or Group IIA metal salt and the molar ratio of acetic acid to acetic anhydride in the vapor fraction removed from the flash separation zone is greater than or equal to 1.

22 Claims, No Drawings

PROCESS FOR THE CO-PRODUCTION OF ACETIC ACID AND ACETIC ANHYDRIDE

This application is the U.S. national phase of International Application No. PCT/EP2014/054398 filed 6 Mar. 2014 which designated the U.S. and claims priority to European Patent Application No. 13158258.7 filed Mar. 7, 2013, the entire contents of each of which are hereby incorporated by reference.

The present invention relates to a continuous process for the co-production of acetic acid and acetic anhydride. In particular, the present invention relates to the co-production of acetic acid and acetic anhydride by the carbonylation of methyl acetate, dimethyl ether or a mixture thereof.

Acetic anhydride and mixtures thereof with acetic acid may be produced by the carbonylation of methyl acetate, dimethyl ether or a mixture thereof under substantially anhydrous conditions in the presence of a Group VIII metal catalyst such as rhodium, and methyl iodide. In such a liquid phase carbonylation process, the crude mixture of acetic anhydride and acetic acid may be recovered by withdrawing the liquid reaction composition from a carbonylation reactor and introducing the withdrawn liquid reaction composition to a flash separation zone to produce a vapour fraction comprising acetic acid, acetic anhydride and methyl iodide and a liquid fraction comprising acetic anhydride and catalyst. The vapour fraction may then be passed to one or more distillation stages to recover acetic anhydride and acetic acid products whilst the liquid fraction is typically recycled to the reactor. Acetic anhydride has a higher boiling point than acetic acid and, in general, acetic acid is more volatile than acetic anhydride, thus the recovery of acetic anhydride in preference to acetic acid remains difficult.

The use of Group IA and/or Group IIA metal salts as catalyst promoters for rhodium catalysts in processes for the co-production of acetic acid and acetic anhydride is known. Thus, U.S. Pat. No. 6,541,666 describes a process for the co-production of acetic anhydride and acetic acid by introducing a carbonylatable feedstock comprising methyl acetate and/or dimethyl ether to a carbonylation reactor in which there is maintained a liquid reaction composition comprising acetic anhydride, acetic acid, rhodium carbonylation catalyst, alkyl iodide co-catalyst and an iodide salt promoter consisting essentially of an alkali metal iodide and/or alkaline earth metal iodide, contacting said carbonylatable feedstock with carbon monoxide in said liquid reaction composition to produce acetic acid and acetic anhydride and introducing to the carbonylation reactor methyl formate and/or formic acid in the range from 0.1 to 20 wt % of the total feed of liquid components to the reactor.

WO 2007/145795 discloses a process for the production of acetic acid or a mixture of acetic acid and acetic anhydride in the liquid phase. The catalyst system disclosed in WO 2007/145795 comprises a promoter component which may be (1) an inorganic salt, such as lithium iodide, or an iodide salt of a quaternary organophosphorus or organonitrogen compound, or (2) an inorganic compound or an organophosphorus or organonitrogen compound which forms an iodide salt in the carbonylation zone.

WO 99/55658 discloses a process for the manufacture of acetic anhydride in the liquid phase. The catalyst system disclosed in WO 99/55658 comprises a promoter component which may be (1) an inorganic salt, such as lithium iodide, or an iodide salt of a quaternary organophosphorus or organonitrogen compound, or (2) an inorganic compound or an organophosphorus or organonitrogen compound which forms an iodide salt in the carbonylation zone.

CH 152249 describes the use of alkali or alkaline earth acetates to separate acetic anhydride and acetic acid in aqueous or non-aqueous solution. CH 152249 does not disclose a process for the co-production of acetic acid and acetic anhydride.

It is known that acetone is formed as an undesirable by-product during processes for the co-production of acetic anhydride and acetic acid by continuous carbonylation processes. Typically, acetone can build up in the reactor and/or in process recycle streams comprising methyl acetate and methyl iodide and may lead to further undesirable by-products such as tars and/or reduction of the overall process efficiency. Several processes are known for separating acetone from mixtures of acetone, methyl acetate and methyl iodide.

Thus, U.S. Pat. No. 4,717,454 describes a process for removing by-product acetone from reaction mixtures obtained by carbonylation of methyl acetate and/or dimethyl ether in which the by-product acetone is subjected to condensation at temperatures of 50° C. to 250° C. under pressures of 0.01 to 150 bar so as to obtain predominantly higher boiling secondary products to be distillatively separated in a successive distillation zone.

It has been observed that in processes for the carbonylation of methyl acetate and/or dimethyl ether to co-produce acetic anhydride and acetic acid, the concentration of acetic anhydride in the reactor influences the formation of undesirable by-products. Without wishing to be bound by theory, it is believed that in such carbonylation processes, some of the acetic anhydride in the reactor decomposes to form acetone and carbon dioxide. Thus, increasing the concentration of acetic anhydride in the reactor generally results in a corresponding and undesirable increase in by-product formation. However, a decrease in the concentration of acetic anhydride in the reactor produces an undesirable decrease in the acetic anhydride production rate.

Acetic anhydride has a higher boiling point than acetic acid and, in general, acetic acid is more volatile than acetic anhydride. Thus, the recovery of acetic anhydride in preference to acetic acid remains difficult. However, it is advantageous to recover as much acetic anhydride as possible relative to acetic acid as acetic anhydride is the more economically valuable product.

It may additionally be desirable to maintain flexibility in the co-production of acetic acid and acetic anhydride so that the relative quantities of either the acetic acid product or the acetic anhydride product can be readily varied. Operationally, it may desirable to maintain a continuous production of acetic acid in excess of the quantity of acetic acid that may be used for esterification with methanol in the preparation of methyl acetate which may be used as a feedstock to the carbonylation process. Such an excess of acetic acid may be used to maintain a sufficient flow of acetic acid through an acetic acid purification system, such that sufficient loading is maintained on the purification system to satisfy certain operational thresholds and/or to ensure that said purification system would not be required to be started up in response to an increase in the amount of acetic acid output under certain circumstances, such as process start-up or process interruptions, as well as being able to respond to changes in relative demand for the two products.

It would therefore be desirable to provide an improved process for the co-production of acetic acid and acetic anhydride in which the production of acetic anhydride is increased and without the need to increase the concentration of acetic anhydride in the reaction zone. It would also be desirable to increase acetic anhydride production whilst suppressing or at least maintaining the rate of formation of by-products.

Accordingly, the present invention provides a continuous process for the co-production of acetic acid and acetic anhydride which comprises the steps of:

(a) contacting in a reaction zone carbon monoxide with a liquid reaction composition comprising methyl acetate, dimethyl ether or a mixture thereof, a Group VIII metal catalyst, methyl iodide, acetic acid, acetic anhydride, water in a concentration of 0.1 wt % or less;

(b) withdrawing liquid reaction composition from the reaction zone and introducing at least a portion of the withdrawn liquid reaction composition into a flash separation zone; and (c) removing from the flash separation zone a vapour fraction comprising acetic anhydride, acetic acid and methyl iodide and a liquid fraction comprising acetic anhydride, and Group VIII metal catalyst;

wherein at least one of the liquid reaction composition and the withdrawn liquid reaction composition introduced into the flash separation zone comprises at least one metal salt selected from salts of Group IA and Group IIA metals and the molar ratio of acetic acid to acetic anhydride in the vapour fraction removed from the flash separation zone is maintained at greater than or equal to 1, preferably greater than or equal to 1.2.

Advantageously, it has been found that by maintaining the molar ratio of acetic acid to acetic anhydride in the vapour fraction removed from the flash separation zone at greater than or equal to 1, preferably greater than or equal to 1.2, the net production of acetic anhydride may be increased whilst maintaining the concentration of acetic anhydride in the carbonylation reaction zone at a predetermined value and without a corresponding increase in by-product formation.

Typically, methyl acetate for use as reactant in processes for the co-production of acetic anhydride and acetic acid is generated by esterification processes of methanol with acetic acid. The acetic acid for such esterification processes may be provided by at least a portion of the acetic acid produced in processes for the co-production acetic anhydride and acetic acid. Thus, a further advantage of the present invention is that by maintaining the molar ratio of acetic acid to acetic anhydride in the vapour fraction removed from the flash separation zone at greater than or equal to 1 sufficient acetic acid is produced (at least 1 mole acetic acid) so as to be available for use in esterification processes to generate methyl acetate from methanol and acetic acid reactants; preferably, by maintaining the molar ratio of acetic acid to acetic anhydride in the vapour fraction removed from the flash separation zone at greater than or equal to 1.2 sufficient acetic acid is produced so as to be available for use in esterification processes to generate methyl acetate from methanol and acetic acid reactants whilst maintaining an amount of acetic acid that may optionally recovered as a product per se and/or be passed through an acetic acid purification system to maintain continuous operation of said acetic acid purification system.

In accordance with the present invention, carbon monoxide is contacted in a reaction zone with a liquid reaction composition comprising methyl acetate, dimethyl ether or a mixture thereof, a Group VIII metal catalyst, alkyl iodide, acetic acid, acetic anhydride, water in a concentration of 0.1 wt % or less.

Carbonylation of methyl acetate, dimethyl ether or mixtures thereof with carbon monoxide takes place in a reaction zone. It is to be understood that the reaction zone can be comprised of a single reaction zone or a plurality of reaction zones.

The reaction zone may comprise one or more pressure vessels which may be provided with means for agitation.

Suitably, the reaction zone is maintained at elevated temperature and pressure such as at a temperature of from 150 to 220° C., preferably of from 175 to 200° C. and at a total pressure of from 1000 kPa to 10000 kPa (10 to 100 bara), preferably at a total pressure of from 2000 to 5000 kPa (20 to 50 bara).

Carbon monoxide used in the present invention may be used as an essentially pure feed, preferably at least 95% pure but inert diluents such as carbon dioxide, nitrogen, methane and inert gases may be present, if desired. Alternatively, the carbon monoxide may be used as a mixture with hydrogen, for example a mixture of carbon monoxide and from >0 to 10 vol % hydrogen.

Methyl acetate, dimethyl ether or a mixture thereof may be continuously fed to the reaction zone. It will, of course be understood that dimethyl ether is converted to methyl acetate in the carbonylation reaction so that it may be considered a methyl acetate precursor.

The total concentration of methyl acetate and dimethyl ether in the liquid reaction composition is suitably maintained in the range from about 5 to about 30% by weight, preferably in the range from about 10 to about 20% by weight. Suitably, the concentration of methyl acetate in the liquid reaction composition is maintained in the range from about 5 to about 30% by weight, preferably in the range from about 10 to about 20% by weight.

Carbonylation of methyl acetate and/or dimethyl ether is facilitated by the use of any suitable Group VIII metal catalyst, such as a rhodium or an iridium catalyst. Preferably, the Group VIII metal catalyst is a rhodium catalyst. Any soluble rhodium catalyst useful in the carbonylation of methyl acetate or dimethyl ether may be used in the present invention. The source of rhodium may be, for example, a simple inorganic salt such as rhodium (III) chloride, rhodium (III) chloride trihydrate, rhodium (III) bromide, or rhodium (III) iodide; a carbonyl or organometallic complex of rhodium, or a co-ordination complex, including, for example $[Rh(CO)_2Cl]_2$, $[Rh(CO)_2I]_2$, $[Rh(Cod)Cl]_2$, rhodium (III) acetate, rhodium dicarbonylacetylacetonate, $RhCl_3(PPh_3)_3$ and $RhCl(CO)(PPh_3)_2$.

The amount of the catalyst is not critical and can vary over a wide range. Typically, however, the concentration of rhodium metal present in the liquid reaction composition in the reaction zone is in the range of about 50 to about 2000 ppm, for example in the range of about 100 to about 1000 ppm.

In accordance with the present invention, at least one of the liquid reaction composition and the withdrawn liquid reaction composition introduced into the flash zone comprises at least one metal salt selected from salts of Group IA and IIA metal salts. Thus, suitably, a metal salt may be present in, or added to, a liquid reaction composition in a reaction zone or it may be added to the liquid reaction composition after withdrawal from the reaction zone and prior to its introduction into the flash separation zone. Preferably, the liquid reaction composition in the reaction zone comprises at least one metal salt.

For the avoidance of doubt, the elements of Group IA of the Periodic Table of the Elements are lithium, sodium, potassium, rubidium, cesium and francium. The elements of Group IIA are beryllium, magnesium, calcium, strontium, barium and radium.

The metal salt may be any Group IA or Group IIA metal salt which dissolves in the liquid reaction composition or is convertible to a soluble form therein. Suitably, the metal salt may be a Group IA or a Group IIA metal acetate or a Group IA or Group IIA metal halide for example a Group IA or a Group IIA metal iodide.

The metal salt may be added as a solid or as a solution in a solvent compatible with the liquid reaction composition, for example a solvent such as acetic acid.

In an embodiment of the present invention, the metal salt is a lithium salt, such as at least one lithium salt selected from lithium acetate and a lithium halide, for example lithium iodide.

In a further embodiment, the liquid reaction composition in the reaction zone comprises a metal salt which is a lithium salt, such as at least one lithium salt selected from lithium acetate and a lithium halide, for example lithium iodide.

It has now been observed that the presence of at least one Group IA or IIA metal salt in liquid reaction compositions for the co-production of acetic acid and acetic anhydride has the effect of enhancing the volatility of acetic anhydride relative to acetic acid. Thus, in a process in which a liquid reaction composition comprises at least one Group IA or IIA metal salt and the liquid reaction composition is introduced into a flash separation zone, relatively more acetic anhydride will be present in the vapour fraction removed from the flash separation zone compared to the amount of acetic anhydride in the vapour fraction obtained in a process wherein no Group IA or IIA metal salt is present in the liquid reaction composition.

The capability of a metal salt to enhance the separation of acetic anhydride relative to acetic acid in a flash separation zone can be determined from the ratio of the flash factors of acetic anhydride and acetic acid. The flash factor (FF) of a component can be determined in accordance with the following equation:

$$FF \text{ (component)} = \frac{\text{(mass of component in flash vapour} \times \text{mass flow rate of flash vapour)}}{\text{(mass of component in liquid reaction composition to flash} \times \text{mass flow rate of liquid reaction composition to flash)}}$$

wherein 'component' is either acetic acid or acetic anhydride.

Flash factor ratios are calculated from FF (acetic acid)/FF (acetic anhydride).

Thus, the lower the value of the ratio of the flash factors, the lower the concentration of acetic anhydride that is required in the reaction zone to achieve a molar ratio of acid:anhydride of greater than or equal to 1, that is ≥1:1, preferably a molar ratio of acid:anhydride of greater than or equal to 1.2, that is ≥1.2:1.

Suitably, the flash factor ratio is in the range of about 0.2 to about 1.4, such as in the range of about 0.3 to about 1.4 or in the range of about 0.2 to about 1.0, for example in the range of about 0.3 to about 1.0, in the range of about 0.2 to about 0.75 or in the range of about 0.3 to about 0.75.

The amount of a metal salt employed according to the present invention should be within the solubility limit of the salt in the liquid reaction composition and be an effective amount sufficient to achieve a molar ratio of acetic acid to acetic anhydride in the vapour fraction from the flash separation zone of greater than or equal to 1, preferably greater than or equal to 1.2.

Suitably, the Group IA and IIA metal salt, preferably a Group IA metal salt, is present in the liquid reaction composition at a total concentration in the range of greater than 0 to about 14000 ppm of Group IA or Group IIA metal, for example in the range of about 1000 to about 6000 ppm, such as in the range of about 1000 to about 5000 ppm.

In an embodiment of the present invention, the metal salt employed is a Group IA metal salt, for example a lithium salt, such as lithium acetate or lithium iodide and the concentration of the lithium salt in a liquid reaction composition is in the range from greater than zero to about 14000 ppm Li, for example in the range of about 1000 to about 6000 ppm Li, such as in the range of about 1000 to about 5000 ppm Li.

Advantageously, the process of the present invention allows increased production of acetic anhydride without requiring a corresponding increase in the concentration of acetic anhydride in the reaction zone. The higher the concentration of the Group IA or IIA metal present in the liquid reaction composition, the lower the concentration of acetic anhydride in the reaction zone required to maintain a molar ratio of acetic acid:acetic anhydride in the flash vapour fraction of greater than or equal to 1 (that is ≥1:1), preferably greater than or equal to 1.2 (that is ≥1.2:1).

Desirably, the concentration of acetic anhydride in the liquid reaction composition in the reaction zone is maintained in the range of about 5 to about 35% by weight, for instance in the range of about 5 to about 30% by weight, such as in the range of about 5 to about 25% by weight, for example in the range of about 10 to about 25% by weight.

In an embodiment of the present invention, the flash factor ratio is in the range of about 0.2 to 1.4, for example about 0.3 to about 1.0, such as in the range of about 0.3 to about 1.0, preferably in the range of about 0.3 to about 0.75 and the concentration of acetic anhydride in the liquid reaction composition in the reaction zone is maintained in the range of about 5 to about 30% by weight such as in the range of about 5 to about 25% by weight, for example about 10 to about 25% by weight.

In a further embodiment, the concentration of acetic anhydride present in the liquid reaction composition in the reaction zone is maintained in the range of about 5 to about 30% by weight such as in the range of about 5 to about 25% by weight, for example about 10 to about 25% by weight and the total concentration of the Group IA and Group IIA metal salt is in the range of about greater than zero to about 14000 ppm of Group IA and Group IIA metal, for example about 1000 to about 13500 ppm of Group IA and Group IIA metal.

The liquid reaction composition in the reaction zone may additionally comprise one or more promoters for the Group VIII metal catalyst, for example one or more promoters for a rhodium catalyst. Suitable promoters include (i) an iodide salt of a quaternary organophosphorus or organonitrogen compound or (ii) an inorganic iodide salt such as lithium iodide or (iii) an inorganic salt or an organonitrogen or organophosphorus compound which forms an iodide salt in the liquid reaction composition.

Suitable iodide salts of a quaternary organophosphorus or organonitrogen compound include tetraalkylphosphonium iodides, tetraalkylammonium iodides, triphenyl(alkyl)phosphonium iodides and N,N'-dialkylimidazolium iodides wherein the alkyl groups contain up to 8 carbon atoms.

Examples of N,N'-dialkylimidazolium iodides include 1,3-dialkyl-4-alkylimidazolium iodides wherein the alkyl groups contain up to 8 carbon atoms, preferably methyl or ethyl alkyl groups.

A portion or all of a promoter which is an inorganic salt may be fed as a salt which forms an iodide salt in the liquid reaction composition. Thus, the promoter may be provided initially, for example in the form of an acetate, hydroxide, chloride or a bromide. Organophosphorus- or organonitrogen-containing promoters may be provided as compounds in which the phosphorus or nitrogen atoms are trivalent, for example tributylphosphine, tributylamine, imidazole and N-methylimidazole, which are quaternised by the methyl iodide present in the liquid reaction composition.

The amount of the promoter in the liquid reaction composition may be varied, depending on a variety of factors, particularly on the particular promoter used. Suitably, the amount of an organophosphorus or an organonitrogen-containing promoter may be present in the liquid reaction composition in amounts such that the molar ratio of promoter to catalyst is at least 0.5:1, for example in the range 0.5:1 to $10^5$:1.

Where it is desired to employ a Group IA or IIA metal salt as promoter, the metal salt is present in the liquid reaction composition in the reaction zone in a concentration so as to achieve a molar ratio of acetic acid to acetic anhydride in the vapour fraction from the flash separation zone of greater than or equal to 1, preferably greater than or equal to 1.2.

Methyl iodide may be present in the liquid reaction composition in the reaction zone in an amount of from about 1 to about 30% by weight, for example of from about 5 to about 20% by weight.

Acetic acid may be maintained in the liquid reaction composition in the reaction zone in an amount of from about 15 to about 50% by weight, such as of from about 20 to about 50% by weight, for example of from about 20 to about 30% by weight.

Suitably, the liquid reaction composition comprises acetic anhydride maintained at a concentration of 5 to 35% by weight, such as 5 to 25% by weight, acetic acid at a concentration of 20 to 50% by weight and balance of methyl acetate, methyl iodide, metal salt, such as a lithium salt and Group VIII metal catalyst and optionally one or more promoters for the Group VIII metal catalyst, such as one or more imidazolium salts.

Suitably, the liquid reaction composition comprises acetic anhydride maintained at a concentration of 5 to 35% by weight, such as 5 to 25% by weight, acetic acid at a concentration of 20 to 50% by weight and balance of methyl acetate, methyl iodide, metal salt, such as a lithium salt and Group VIII metal catalyst and optionally one or more promoters for the Group VIII metal catalyst, such as one or more imidazolium salts and the liquid reaction composition is introduced into the flash separation zone at a temperature in the range of from 175° C. to 200° C. and at a pressure in the range of 20 to 50 barg.

The carbonylation reaction is carried out in the reaction zone under substantially anhydrous conditions. Thus, the concentration of water present in the liquid reaction composition is less than 0.1% by weight. Preferably, there is a complete absence of water in the liquid reaction composition present in the reaction zone.

In an embodiment of the present invention the continuous process for the co-production of acetic acid and acetic anhydride comprises the steps of:

(a) contacting in a reaction zone carbon monoxide with a liquid reaction composition comprising methyl acetate, dimethyl ether or a mixture thereof, a rhodium catalyst, methyl iodide, acetic acid, acetic anhydride in a concentration of about 5 to about 25% by weight, water in a concentration of 0.1 wt % or less;

(b) withdrawing liquid reaction composition from the reaction zone and introducing at least a portion of the withdrawn liquid reaction composition into a flash separation zone; and (c) removing from the flash separation zone a vapour fraction comprising acetic anhydride, acetic acid and methyl iodide and a liquid fraction comprising acetic anhydride, rhodium catalyst;

wherein at least one of the liquid reaction composition and the withdrawn liquid reaction composition introduced into the flash separation zone comprises at least one metal salt selected from salts of Group IA and Group IIA metals and the molar ratio of acetic acid to acetic anhydride in the vapour fraction removed from the flash separation zone is maintained at greater than or equal to 1, preferably greater than or equal to 1.2.

In the process of the present invention liquid reaction composition is withdrawn from the reaction zone and is introduced into a flash separation zone wherein the liquid reaction composition is separated into a vapour fraction and a liquid fraction.

The rate of liquid reaction composition removal may be controlled by a flashing valve, across which the pressure is reduced from that in the reaction zone to that in the flash separation zone.

To increase the depth of flash, the temperature of the liquid reaction composition withdrawn from the reaction zone is suitably increased prior to introduction into the flash separation zone by means of, for example a heater.

Suitably, the liquid reaction composition is introduced into the flash separation zone at a temperature of about 10° C. to about 20° C. higher than the temperature at which it was withdrawn from the reaction zone.

The flash separation zone may comprise an adiabatic flash vessel. Alternatively, the flash separation zone may be provided with one or more heating means.

The conditions of temperature and pressure in the flash separation zone may be varied and depend upon such factors as the relative amounts of acetic anhydride and acetic acid present in the liquid reaction composition. The conditions are selected so that the acetic anhydride present in the liquid reaction composition is partitioned between the vapour and liquid fractions. Desirably, the flash separation zone is operated at a temperature which is above the freezing point of the liquid fraction but at a temperature below which all of the liquid reaction composition is vapourised and which preferably avoids or mitigates undesired breakdown of the components of the liquid reaction composition.

Suitably, the flash separation zone is operated at a temperature of from about 50° C. to about 400° C., for example of from about 50 to about 300° C.

The flash separation zone may be operated at a range of pressures and a specific operating pressure may be selected so as to provide the desired partitioning of acetic anhydride between the vapour and liquid fractions. The flash separation zone may be operated at subatmospheric, atmospheric or superatmospheric pressure and suitably is operated at a pressure of zero barg to 10 barg, for example at a pressure of zero barg to 3 barg.

The vapour fraction removed from the flash separation zone comprises acetic anhydride, acetic acid and low boiling components such as methyl iodide, methyl acetate and/or dimethyl ether. The vapour fraction may also contain minor amounts of by-products such as acetone.

Suitably, the molar ratio of acetic acid:acetic anhydride in the vapour fraction removed from the flash separation zone is maintained in the range 1 to 3.5:1, such as in the range of from 1 to 3:1, preferably in the range 1.2 to 3.5:1, more in the range of from 1.2 to 3:1, for example in the range 1.2 to 2.8:1, for instance in the range 1.2 to 2.5:1, such as in the range 1.2 to 1.5:1. In one specific embodiment of the present invention, the molar ratio of acetic acid to acetic anhydride in the vapour fraction removed from the flash separation zone is maintained at about 1:1.

In an embodiment of the present invention, the molar ratio of acetic acid:acetic anhydride in the vapour fraction removed from the flash separation zone is in the range of 1 to 3:1, preferably in the range of 1.2 to 3:1, and the concentration of acetic anhydride in the liquid reaction composition is maintained in the range of about 5 to about 35% by weight, for example in the range of about 5 to about 25% by weight.

In another embodiment of the present invention, the molar ratio of acetic acid:acetic anhydride in the vapour fraction removed from the flash separation zone is in the range of 1 to 3:1, preferably in the range of 1.2 to 3:1, and the liquid reaction composition comprises acetic anhydride maintained at a concentration of 5 to 35% by weight, such as 5 to 25% by weight, acetic acid at a concentration of 20 to 50% by weight and balance of methyl acetate, methyl iodide, metal salt, such as a lithium salt and Group VIII metal catalyst components.

In another embodiment of the present invention, the molar ratio of acetic acid:acetic anhydride in the vapour fraction removed from the flash separation zone is in the range 1 to 3:1, preferably in the range of 1.2 to 3:1, and the flash factor ratio is in the range of about 0.2 to about 1, preferably in the range of about 0.3 to about 1, for example in the range of about 0.3 to about 0.75. In this embodiment, the concentration of acetic anhydride in the liquid reaction composition is suitably in the range of from about 5 to about 25% by weight.

The liquid fraction removed from the flash separation zone comprises a solution of the catalyst in acetic anhydride or a mixture of acetic anhydride and acetic acid. The liquid fraction will, in general, also comprise the metal salt and/or catalyst promoters.

Suitably, at least a portion of the liquid fraction from the flash separation zone is recycled to the reaction zone.

Suitably, at least a portion of the vapour fraction from the flash separation zone is passed to a purification zone for separation and recovery of acetic anhydride and acetic acid products.

The purification zone may comprise one or more distillation zones. For example, the purification zone may comprise a first distillation zone in which acetic anhydride and acetic acid products are separated from light components, such as methyl iodide and methyl acetate. The light components are removed overhead from the first distillation zone and may be recycled to the reaction zone. The purification zone preferably comprises at least one further distillation zone to separate acetic acid and acetic anhydride products.

Each distillation zone can be any conventional distillation apparatus used in the co-production of acetic anhydride and acetic acid.

In one embodiment of the present invention, acetic acid recovered from a distillation zone, or a portion thereof is supplied to an esterification step wherein it is reacted with methanol to form an esterification product comprising methyl acetate and water and optionally unreacted methanol. Some or all of the water is removed from the esterification product and the remaining esterification product comprising methyl acetate may be fed, as a reactant, to the reaction zone.

The invention will now be illustrated by reference to the following Examples.

REFERENCE EXAMPLE

In this Reference Example a liquid reaction composition comprising acetic anhydride and acetic acid was produced by contacting in a reaction zone methyl acetate, methanol, rhodium catalyst, methyl iodide and an imidazolium salt with carbon monoxide under substantially anhydrous conditions at a temperature of about 190° C. and a pressure of about 35 barg

EXAMPLES 1 TO 3

In these Examples, liquid reaction compositions were produced in accordance with the Reference Example except that varying amounts of lithium acetate were added to the reaction zone. Liquid reaction composition was withdrawn from the reaction zone and introduced to a flash separation zone operated at about 135° C. and at a pressure of about 2 barg. A vapour fraction comprising acetic anhydride and acetic acid was removed as an overhead from the flash separation zone and a liquid fraction comprising acetic anhydride, acetic acid and catalyst components was removed therefrom as a base stream.

The mass of acetic acid and acetic anhydride present in the flash vapour and liquid fractions and in the withdrawn liquid reaction composition were determined by gas chromatography. The flow rates of the flash vapour and liquid fractions and the withdrawn liquid reaction composition were determined using an orifice meter.

The capability of the metal salt to enhance the separation of acetic anhydride relative to acetic acid in the flash separation zone was determined from the ratio of the flash factors of acetic acid to acetic anhydride. The results obtained are given in Table 1 below.

TABLE 1

| Example | Li (ppm) | Flash factor ratio |
| --- | --- | --- |
| Reference | 0 | 1.45 |
| 1 | 1000 | 1.14 |
| 2 | 3000 | 0.87 |
| 3 | 4000 | 0.75 |

As can be seen from Table 1, the results demonstrate that the addition of the metal salt decreases the flash factor ratio of acetic acid to acetic anhydride and thus more acetic anhydride relative to acetic acid may be separated in the flash separation zone.

EXAMPLE 4

A liquid reaction composition comprising methyl acetate, acetic acid, methyl iodide, acetic anhydride, Group VIII metal catalyst, catalyst promoter and optionally lithium iodide was continuously fed to a commercial scale reactor. Carbon monoxide gas contacted the reaction composition in the reactor by means of a sparging device to produce acetic anhydride and acetic acid. The liquid reaction mixture was continuously withdrawn from the reactor and passed via a flashing valve to a flash zone operated at a reduced pressure compared to the reactor to form an overhead vapour fraction comprising acetic acid and acetic anhydride and a liquid fraction comprising acetic acid and the catalyst components. The amounts of acetic acid, acetic anhydride produced (tpd (tonnes per day)) in the presence and absence of the metal salt are shown in Table 2.

TABLE 2

| Li (ppm) | Acetic Acid (tpd) | Acetic Anhydride (tpd) | Molar ratio of acetic acid:acetic anhydride | % increase in acetic anhydride |
|---|---|---|---|---|
| 0 | 285 | 258 | 1.88 | — |
| 1500 | 346 | 335 | 1.25 | 29 |

The results of Table 2 clearly demonstrate that the present invention provides for an increased production rate of acetic anhydride relative to acetic acid without necessitating an increase in the concentration of acetic anhydride in the reactor.

EXAMPLE 5

This Example illustrates the concentration of lithium required, whilst maintaining acetic anhydride at different concentrations in a reactor, to maintain a molar ratio of acetic acid to acetic anhydride of 1 in the flash vapour fraction. Liquid reaction compositions comprising acetic anhydride (5-35% by weight), acetic acid (20-50% by weight) and balance (45% by weight) of methyl acetate, methyl iodide, lithium salt and Group VIII metal catalyst components were continuously contacted with carbon monoxide under substantially anhydrous conditions in the reactor operated at a temperature of about 190° C. and at a pressure of about 36 barg to co-produce acetic anhydride and acetic acid. The reaction compositions were supplied via a flashing valve to a flash vessel operated at a temperature of about 135° C. and at pressure of about 2 barg and separated to produce a vapour fraction comprising acetic anhydride and acetic acid and a liquid fraction comprising acetic acid, lithium and catalyst components.

TABLE 3

Molar Ratio = 1

| Acetic Anhydride (% by weight in reactor) | Li (ppm) | Flash Factor Ratio |
|---|---|---|
| 5 | 13500 | 0.08 |
| 11 | 12347 | 0.15 |
| 15 | 11096 | 0.22 |
| 21 | 8858 | 0.36 |
| 25 | 7076 | 0.49 |
| 31 | 3946 | 0.76 |
| 35 | 1706 | 1.03 |

As can be seen from Table 3, for a given standing concentration of acetic anhydride in the reactor, the addition of a metal salt and a molar ratio of acetic acid to acetic anhydride in the flash vapour of 1 increases the amount of acetic anhydride produced relative to acetic acid, as indicated by the reduced flash factor ratios.

EXAMPLE 6

Example 5 was repeated utilising a combination of metal salt and molar ratios of acetic acid to acetic anhydride of 1.2, 1.8, 2.4 and 3. The results are shown in Tables 4 to 7 respectively. Tables 4 to 7 indicate, for a given standing concentration of acetic anhydride in the reactor, the amount of metal salt required to increase the amount of acetic anhydride produced relative to acetic acid, as indicated by the reduced flash factor ratios, at specified molar ratios of acetic acid to acetic anhydride in the flash vapour.

TABLE 4

Molar Ratio = 1.2

| Acetic Anhydride (% by weight in reactor) | Li (ppm) | Flash Factor Ratio |
|---|---|---|
| 5 | 13129 | 0.10 |
| 11 | 11839 | 0.18 |
| 15 | 10378 | 0.26 |
| 21 | 7813 | 0.44 |
| 25 | 5835 | 0.58 |
| 31 | 2574 | 0.91 |
| 35 | 595 | 1.24 |

TABLE 5

Molar ratio = 1.8

| Acetic Anhydride (% by weight in reactor) | Li (ppm) | Flash Factor Ratio |
|---|---|---|
| 5 | 12220 | 0.15 |
| 11 | 10377 | 0.26 |
| 15 | 8364 | 0.40 |
| 21 | 5068 | 0.65 |
| 25 | 2818 | 0.88 |
| 31 | 154 | 1.36 |

TABLE 6

Molar Ratio = 2.4

| Acetic Anhydride (% by weight in reactor) | Li (ppm) | Flash Factor Ratio |
|---|---|---|
| 5 | 11342 | 0.20 |
| 11 | 9012 | 0.35 |
| 15 | 6566 | 0.52 |
| 21 | 2906 | 0.87 |
| 25 | 860 | 1.18 |
| 31 | 280 | 1.82 |

TABLE 7

Molar Ratio = 3

| Acetic Anhydride (% by weight in reactor) | Li (ppm) | Flash Factor Ratio |
|---|---|---|
| 5 | 10496 | 0.26 |
| 11 | 7741 | 0.44 |
| 15 | 4982 | 0.66 |
| 21 | 1326 | 1.08 |
| 23 | 465 | 1.26 |

The invention claimed is:
1. A continuous process for the co-production of acetic acid and acetic anhydride which comprises the steps of:
(a) contacting in a reaction zone carbon monoxide with a liquid reaction composition comprising methyl acetate or a mixture of dimethyl ether and methyl acetate, a Group VIII metal catalyst, methyl iodide, acetic acid, acetic anhydride, water in a concentration of 0.1 wt % or less;
(b) withdrawing liquid reaction composition from the reaction zone and introducing at least a portion of the withdrawn liquid reaction composition into a flash separation zone; and
(c) removing from the flash separation zone a vapour fraction comprising acetic anhydride, acetic acid and methyl iodide and a liquid fraction comprising acetic anhydride, and Group VIII metal catalyst;

wherein the liquid reaction composition introduced into the flash separation zone comprises at least one metal salt selected from salts of Group IA and Group IIA metals and the molar ratio of acetic acid to acetic anhydride in the vapour fraction removed from the flash separation zone is maintained in the range 1.2 to 3:1; and wherein the process further comprises conducting at least a portion of the acetic acid of the vapour fraction to an esterification process in which the acetic acid is esterified with methanol to form methyl acetate, and conducting at least a portion of the methyl acetate so formed to the reaction zone for reaction in step (a).

2. A process according to claim 1, wherein the molar ratio of acetic acid to acetic anhydride in the vapour fraction removed from the flash separation zone is maintained in the range 1.2 to 2.5:1.

3. A process according to claim 1, wherein the molar ratio of acetic acid to acetic anhydride in the vapour fraction removed from the flash separation zone is maintained in the range 1.2 to 1.5:1.

4. A process according to claim 1, wherein acetic anhydride is maintained in the liquid reaction composition at a concentration in the range of about 5 to about 35% by weight.

5. A process according to claim 1, wherein the metal salt is a Group IA metal salt.

6. A process according to claim 1, wherein the Group IA and Group IIA metal is present in the liquid reaction composition at a total concentration in the range greater than zero to about 14000 ppm.

7. A process according to claim 1, wherein the metal salt is present in the liquid reaction composition in the reaction zone.

8. A process according to claim 1, wherein the acetic acid and acetic anhydride have a flash factor ratio in the range of about 0.2 to about 1.4.

9. A process according to claim 1, wherein the Group VIII metal catalyst is a rhodium catalyst.

10. A process according to claim 1, wherein the liquid reaction composition additionally comprises one or more promoters for the Group VII metal catalyst.

11. A process according to claim 1, wherein the liquid reaction composition comprises acetic anhydride maintained at a concentration of 5 to 35% by weight, acetic acid at a concentration of 20 to 50% by weight, and balance of methyl acetate, methyl iodide, metal salt, Group VIII metal catalyst and optionally one or more promoters for the Group VIII metal catalyst.

12. A process according to claim 1, wherein the flash separation zone is operated at a pressure of zero barg to 10 barg.

13. A process according to claim 1, wherein the flash separation zone is operated at a temperature of from about 50° C. to about 400° C.

14. A process according to claim 1, wherein the reaction zone is maintained at a temperature of from 150 to 220° C. and at a total pressure of from 10 to 100 bara.

15. A process according to claim 1, wherein the molar ratio of acetic acid to acetic anhydride in the vapour fraction removed from the flash separation zone is maintained in the range 1.2 to 2.8:1.

16. A process according to claim 1, wherein the metal salt is a lithium salt.

17. A process according to claim 1, wherein a portion of the acetic acid in the vapour fraction is passed through an acetic acid purification system to maintain continuous operation of said acetic acid purification system.

18. A process according to claim 1, wherein the Group IA and Group IIA metal is present in the liquid reaction composition at a total concentration in the range of about 1000 to about 6000 ppm.

19. A process according to claim 1, further comprising increasing the temperature of the liquid reaction composition withdrawn from the reaction zone before it is introduced into the flash separation zone.

20. A process according to claim 1, wherein the acetic acid and acetic anhydride have a flash factor ratio in the range of about 0.3 to about 0.75.

21. A process according to claim 1, further comprising adding metal salt to the liquid reaction composition after withdrawing the liquid reaction composition from the reaction zone but before introducing the liquid reaction composition to the flash separation zone.

22. A process according to claim 1, wherein
the metal salt is a lithium salt;
the liquid reaction composition comprises acetic anhydride maintained at a concentration of 5 to 35% by weight, acetic acid at a concentration of 20 to 50% by weight, and balance of methyl acetate, methyl iodide, lithium salt, Group VIII metal catalyst and optionally one or more promoters for the Group VIII metal catalyst; and
the acetic acid and acetic anhydride have a flash factor ratio in the range of about 0.3 to about 0.75.

* * * * *